(12) United States Patent
Surendran

(10) Patent No.: US 10,426,160 B2
(45) Date of Patent: Oct. 1, 2019

(54) COMPOSITIONS AND METHODS FOR PRESERVING RED BLOOD CELLS AND PLATELETS

(71) Applicant: RYTHRX THERAPEUTICS, LLC, Ann Arbor, MI (US)

(72) Inventor: Narayanan Surendran, Ann Arbor, MI (US)

(73) Assignee: RythRx Therapeutics, LLC, Ann Arbor, MI (US)

( * ) Notice: Subject to any disclaimer, the term of this patent is extended or adjusted under 35 U.S.C. 154(b) by 0 days.

(21) Appl. No.: 16/111,635

(22) Filed: Aug. 24, 2018

(65) Prior Publication Data

US 2018/0360022 A1 Dec. 20, 2018

Related U.S. Application Data

(63) Continuation of application No. 14/905,341, filed as application No. PCT/US2014/046964 on Jul. 17, 2014.

(60) Provisional application No. 61/896,307, filed on Oct. 28, 2013, provisional application No. 61/847,294, filed on Jul. 17, 2013.

(51) Int. Cl.
*A61K 31/519* (2006.01)
*A01N 1/02* (2006.01)
*A61K 31/7064* (2006.01)
*C12N 5/078* (2010.01)

(52) U.S. Cl.
CPC ........... *A01N 1/0226* (2013.01); *A01N 1/021* (2013.01); *A61K 31/519* (2013.01); *A61K 31/7064* (2013.01); *C12N 5/0641* (2013.01); *C12N 5/0644* (2013.01); *C12N 2501/999* (2013.01)

(58) Field of Classification Search
CPC .................................................. A01N 1/0226
See application file for complete search history.

(56) References Cited

U.S. PATENT DOCUMENTS

| 4,123,524 | A | 10/1978 | Townsend et al. |
| 4,675,185 | A | 6/1987 | Kandler et al. |
| 4,769,318 | A | 9/1988 | Hamasaki et al. |
| 4,812,310 | A | 3/1989 | Sato et al. |
| 5,876,676 | A | 3/1999 | Stossel et al. |
| 5,906,915 | A | 5/1999 | Payrat et al. |
| 6,150,085 | A | 11/2000 | Hess et al. |
| 6,221,669 | B1 | 4/2001 | Livesey et al. |
| 8,492,081 | B2 | 7/2013 | Nichols et al. |
| 2005/0208462 | A1 | 9/2005 | Bitensky et al. |
| 2005/0233302 | A1 | 10/2005 | Hess et al. |
| 2010/0068690 | A1* | 3/2010 | Liotta ............... A01N 1/00 435/1.1 |
| 2010/0093609 | A1 | 4/2010 | Hilfinger et al. |
| 2011/0117647 | A1 | 5/2011 | Mayaudon et al. |
| 2011/0229871 | A1 | 9/2011 | Ericson |
| 2012/0225419 | A1 | 9/2012 | Min et al. |

FOREIGN PATENT DOCUMENTS

JP 2006-124405 A 5/2006
WO WO 2004/105483 A1 12/2014

OTHER PUBLICATIONS

Antonelou, Marianna H., et al., "Red blood cell aging markers during storage in citrate-phosphate-dextrose-saline-adenine-glucose-mannitol," *Transfusion* 50:376-389 (2010).
Burger, Patrick, et al., "An improved red blood cell additive solution maintains 2,3-diphosphoglycerate and adenosine triphosphate levels by an enhancing effect on phosphofructokinase activity during cold storage," *Transfusion* 50:2386-2392 (2010).
D'Amici, Gian Maria, et al., "Red blood cell storage in SAGM and AS3: a comparison through the membrane two-dimensional electrophoresis proteome," *Blood Transfus*, 10 Suppl. 2:s46-54 (2012).
Edenbrandt, C.M, et al., "Adenine and guanine nucleotide metabolism during platelet storage at 22 degrees C," *Blood* 76(9):1884-1892 (1990).
Fan et al., Biorganic & Medicinal Chem. Letters, 1997, 7(24): 3107-3112.
Feun, Lynn G., et al., "Phase I Study of Tricyclic Nucleoside Phosphate Using a Five-Day Continuous Infusion Schedule," *Cancer Res* 44:3608-3612 (1984).
Filip, D.J., et al., "The effect of platelet concentrate storage temperature on adenine nucleotide metabolism," *Blood* 45(6):749-756 (1975).
Harberson et al., Chapter 24—Deuterium in Drug Discovery and Development, Annual Reports in Medicinal Chemistry, vol. 46, 2011, pp. 403-417.
International Search Report and Written Opinion of corresponding International Application No. PCT/US2014/046964, dated Oct. 8, 2014 (11 pages).
Macey, Marion, et al., "Evaluation of the Anticoagulants EDTA and Citrate, Theophylline, Adenosine, and Dipyridamole (CTAD) for Assessing Platelet Activation on the ADVIA 120 Hematology System," *Clinical Chemistry* 48(6):891-899 (2002).
Manno, Sumie, et al., "Modulation of Erythrocyte Membrane Mechanical Function by β-Spectrin Phosphorylation and Dephosphorylation," *The Journal of Biological Chemistry* 270(10):5659-5665 (1995).
Meinitzer et al., Therapeutic Drug Monitoring: Feb. 2010—vol. 32—Issue 1—pp. 61-66.
Meyer, Erin K., et al., "Rejuvenation capacity of red blood cells in additive solutions over long-term storage," *Transfusion* 51:1574-1579 (2011).
Prankerd, T.A.J., et al., "Revival of Stored Blood with Guanosine and Its Successful Transfusion," *The Lancet*, 469-471 (1956).
Sparrow, Rosemary L., "Time to revisit red blood cell additive solutions and storage conditions: a role for "omics" analyses," *Blood Transfus*, 10 Suppl 2:s7-11 (2012).

(Continued)

*Primary Examiner* — Svetlana M Ivanova
(74) *Attorney, Agent, or Firm* — Brinks Gilson & Lion; Ryan L. Marshall; Robert Shereda

(57) ABSTRACT

Blood and platelet storage and rejuvenating compositions that include triciribine, triciribine metabolites, triciribine analogs, and mixtures of the same are disclosed. Such compositions can be useful in methods for treating (e.g., storing and rejuvenating) red blood cells and platelets.

17 Claims, 4 Drawing Sheets

(56) References Cited

OTHER PUBLICATIONS

Wolfe, Lawrence C., et al., "Molecular Defect in the Membrane Skeleton of Blood Bank-stored Red Cells," *J. Clin. Invest.* 78:1681-1686 (1986).

* cited by examiner

COMPOSITIONS AND METHODS FOR PRESERVING RED BLOOD CELLS AND PLATELETS

REFERENCE TO EARLIER FILED APPLICATIONS

This application is a continuation of U.S. patent application Ser. No. 14/905,341, filed Jan. 15, 2016, which is a 371 national phase of International Application No. PCT/US2014/046964, filed Jul. 17, 2014, and claims the benefit under 35 U.S.C. § 119(e) of U.S. Provisional Application No. 61/896,307, filed Oct. 28, 2013, and of U.S. Provisional Application No. 61/847,294, filed Jul. 17, 2013, the disclosures of which are incorporated, in their entirety, by this reference.

BACKGROUND

Whole blood is a living tissue that circulates through the heart, arteries, veins and capillaries, carrying nourishment, electrolytes, antibodies, heat and oxygen to the body tissues. Whole blood includes red blood cells (RBCs), white blood cells, and platelets suspended in plasma. If blood is treated to prevent clotting and permitted to stand in a container, RBCs will settle to the bottom of the container, the plasma will remain on top and the white blood cells will form a layer on top of the RBCs. A centrifuge is commonly used to hasten this separation. The platelet-rich plasma is then removed and placed into a sterile bag for further processing to separate, for example, platelets, clotting factors, albumin, immunoglobulins and the like.

The most important component for transfusion needs is the erythrocytes or RBCs, which contain hemoglobin, a complex iron-containing protein that carries oxygen throughout the body and gives blood its red color. The percentage of blood volume that is composed of RBCs is called the "hematocrit." The average hematocrit in the adult male is 47%. There are about one billion RBCs in two or three drops of blood, and, for every 600 RBCs, there are about 40 platelets and one white blood cell.

Bone marrow produces RBCs as enucleated, biconcave discs that are continuously being produced, broken down and destroyed. The biconcave disc shape is crucial to the function of RBCs, presenting a maximal surface area for the capture of oxygen in the lungs and its release in the tissue. The cells are flexible and able to bend in order to traverse the tiny tubules of the capillary beds. Since the cells are enucleated and lack mitochondria, they are unable to carry out cellular repair processes and must rely on anaerobic phosphorylation for energy. After an average of 120 days in the circulatory system, the cells are senescent and are phagocytized by circulating monocytes or the fixed macrophages of the reticulo-endothelial system. However, U.S. Food and Drug Administration licensure for transfusion is limited to a maximum of 42 days (6 weeks) regardless of the age of individual RBCs in the stored preparation.

RBCs are prepared from whole blood by removing the plasma. When transfused into a patient, the hematocrit is raised while an increase in blood volume is minimized, which is especially important to such patients as those with congestive heart failure. The cells are typically suspended in about half the original volume; the preparation is referred to as packed red cells. Patients benefiting most from transfusions of RBCs include those with chronic refractive anemia from disorders such as kidney failure, malignancies, gastrointestinal bleeding or acute blood loss as from trauma or surgery.

Because patients seldom require all of the components of whole blood, it is the usual practice in blood banks to separate the blood into components and transfuse only that portion needed by the patient for a specific condition or disease. This treatment, referred to as "blood component therapy" allows several patients to benefit from each unit of blood. Unfortunately, the separation of blood components for therapy is detrimental to the RBCs, causing a storage lesion characterized by a decrease in ATP, 2,3-diphosphoglycerate (2,3-DPG), an increase in the production of oxygen free radicals and a change in morphology.

Standard solutions for the storage of whole blood include citrate-phosphate-dextrose solution (CPD) and citrate-phosphate-dextrose-adenine solution (CPDA) as components of additive solutions. Citrate or other anticoagulants such as heparin are necessary to prevent clotting. Because blood is a living tissue that maintains metabolic functions even at refrigerated temperatures, it has been considered necessary to provide an energy source such as dextrose. Phosphate ion can be used to buffer the lactate produced from dextrose utilization. Other components of additive solutions include salts and buffers to help maintain physiological plasma pH conditions. Nucleobases such as adenine and nucleosides such as guanosine may also be added.

Improvements in cell preservation solutions over the last 15 years have increased the refrigerated shelf life of whole blood or RBCs from 21 to 42 days. After 42 days, the blood is discarded, since many of the cells have become senescent and would be immediately phagocytized upon transfusion into a recipient. Although the red cells may appear to survive in storage for five or six weeks, they rapidly develop storage lesions characterized by hemolysis and/or biochemical and biomechanical changes that can compromise their survival time and their ability to accept, transport, and unload oxygen to the tissue. For that reason, it is desirable to use the whole blood and blood products within three weeks or less of drawing them from a donor.

The absence of adequate numbers of hemostatically active blood platelets is associated with many disease states, some of which can only be treated by transfusion of blood products containing large numbers of viable platelets. Freshly obtained blood platelets mediate hemostasis by converting, where properly instructed, from discs to spiny pleated spheres that attach to breaks in blood vessels and to other platelets. This process, referred to as platelet activation, is triggered by a variety of different agonists, including thrombin, adenosine diphosphate (ADP), thromboxanes, collagen, von Willebrand's factor, as well as upon contact of platelets with glass.

Current practice permits platelets to be stored no longer than several days, after which the platelets are no longer hemostatically active and are discarded as "outdated." It is estimated that about 15% of procured units of blood are discarded as outdated. As a result of the short platelet shelf life, a large supply of donated blood is required to sustain each patient requiring platelet replacement therapy.

Given the problems of platelet availability, various attempts have been made to preserve platelets for longer periods of time with retention of hemostatic activity. These attempts include using non-glass storage containers as described in U.S. Pat. No. 5,876,676, chemical additives such as those described in U.S. Pat. Nos. 6,221,669 and 8,492,081, as well as cryogenic techniques.

There remains a need for methods and pharmaceutical compositions to preserve platelets. Such methods would permit the preservation of blood platelets with preserved hemostatic activity for longer periods of time than are presently possible.

There also remains a need for a compositions and methods that preserve whole blood or packed red cell suspensions for greater time periods. There is also a need for methods to rejuvenate blood and maintain structure and function of RBC to achieve optimum clinical outcomes.

SUMMARY

In one aspect, a composition for preserving blood is disclosed, including a compound selected from triciribine, a triciribine metabolite, triciribine analogs, and prodrugs and mixtures of the same; and blood.

In one aspect, a composition for preserving platelets is disclosed, including a compound selected from triciribine, a triciribine metabolite, triciribine analogs, and prodrugs and mixtures of the same; and blood.

In some embodiments, the triciribine metabolite is selected from ((2R,3S,4R,5R)-5-(3-amino-5-methyl-1,4,5,6,8-pentaazaacenaphthylen-1(5H)-yl)-3,4-dihydroxytetrahydrofuran-2-yl)methyl dihydrogen phosphate; 3-amino-5-(((2R,3R,4S,5R)-3,4-dihydroxy-5-(hydroxymethyl)tetrahydro-furan-2-yl)amino)-1-methylpyrimido[4,5-c]pyridazin-4(1H)-one; and ((2R,3S,4R,5R)-5-((3-amino-1-methyl-4-oxo-1,4-dihydropyrimido[4,5-c]pyridazin-5-yl)amino)-3,4-dihydroxytetrahydrofuran-2-yl)methyl dihydrogen phosphate.

In some embodiments, the triciribine analog is selected from an amino acid prodrug of TCN and a phosphoramidate prodrug of TCNP. In some embodiments, the compound is triciribine. In some embodiments, the composition also includes an anticoagulant, buffer, additive solution, and combinations of the same. In some embodiments, the compound has one or more deuterium substitutions.

In another aspect, a method of storing blood is disclosed having the steps of contacting red blood cells with a blood storage composition as described herein. In another aspect, a method of rejuvenating blood is disclosed having the steps of contacting red blood cells with a composition as described herein.

In some embodiments, the red blood cells in the methods are packed red blood cells. In some embodiments, the red blood cells are in whole blood.

In another aspect, a method of storing platelets is disclosed having the steps of contacting platelets with a platelet storage composition as described herein. In another aspect, a method of rejuvenating platelets is disclosed having the steps of contacting platelets with a composition as described herein. In some embodiments, the platelets are in whole blood.

DEFINITIONS

Figure 1:
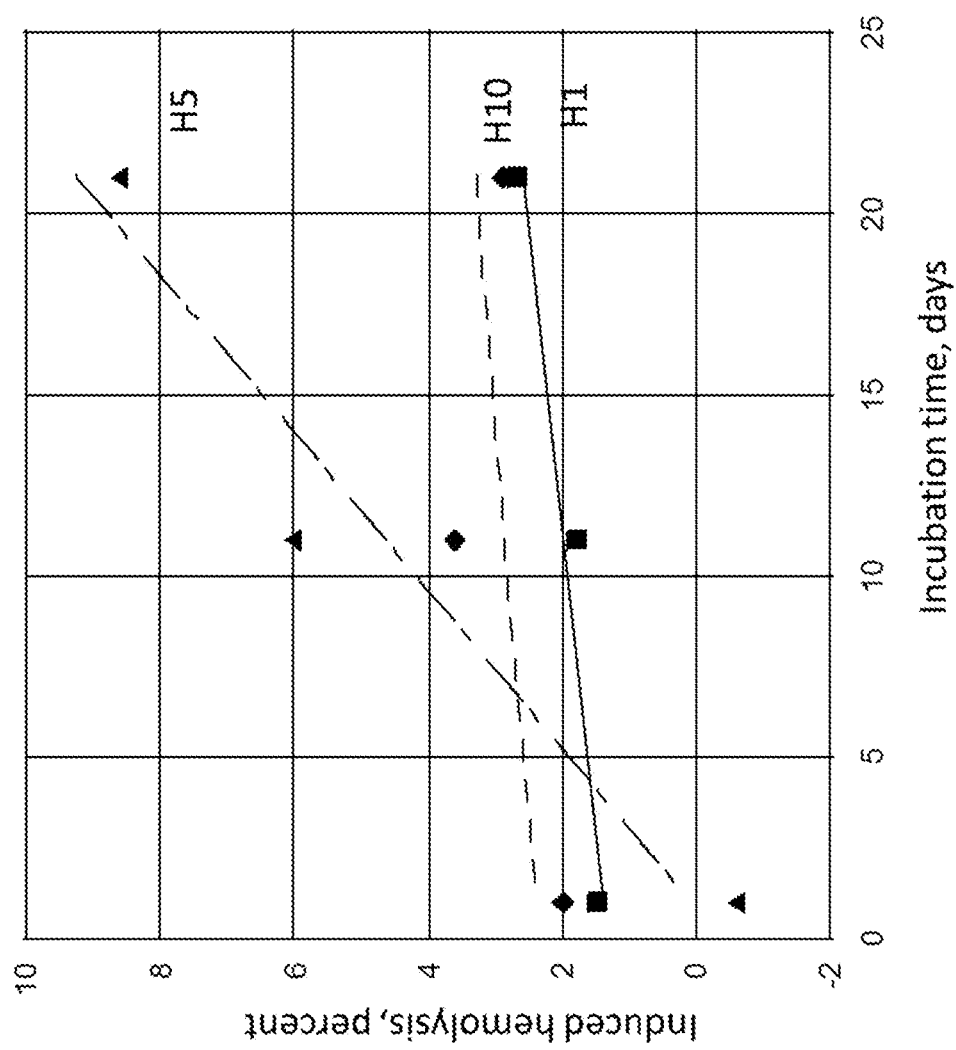
FIG. 1 shows representative hemolysis observations from experiments using embodiments of the invention.

Unless otherwise specified, "a," "an," "the," and "at least one" are used interchangeably and mean one or more than one.

As used herein, the term "comprising," which is synonymous with "including" or "containing," is inclusive, open-ended, and does not exclude additional unrecited elements or method steps.

Also herein, the recitations of numerical ranges by endpoints include all numbers subsumed within that range (e.g., 1 to 5 includes 1, 1.5, 2, 2.75, 3, 3.80, 4, 5, etc.).

The above brief description of various embodiments of the present invention is not intended to describe each embodiment or every implementation of the present invention. Rather, a more complete understanding of the invention will become apparent and appreciated by reference to the following description and claims. Further, it is to be understood that other embodiments may be utilized and structural changes may be made without departing from the scope of the present invention.

As used herein, the term "aliphatic" means a straight or branched, saturated cyclic, saturated or unsaturated acyclic hydrocarbon; and includes $C_1$-$C_{20}$ alkyl, $C_1$-$C_6$ alkyl, $C_2$-$C_4$ alkyl, $C_3$-$C_6$ cycloalkyl, $C_2$-$C_{20}$ alkenyl, $C_2$-$C_6$ alkenyl, $C_2$-$C_4$ alkenyl, and $C_2$-$C_{20}$ alkynyl, $C_2$-$C_6$ alkynyl, $C_2$-$C_4$ alkynyl groups.

As used herein, the term "aryl" means a moiety containing an aromatic ring, and includes phenyl, biphenyl, naphthyl, and the like. For the purposes of the invention, "heteroaryl" means a moiety containing an aromatic ring, where the aromatic ring contains at least one nitrogen atom.

Aryl and heteroaryl are optionally substituted with at least one or more moieties selected from alkyl, alkoxy, haloalkyl, and hydroxyl. The halogen can be fluoro-, chloro, or bromo-.

The term "alkyl," as used herein, unless otherwise specified, includes a saturated straight, branched, or cyclic, primary, secondary, or tertiary hydrocarbon of for example $C_1$ to $C_{24}$, and specifically includes methyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. The alkyl is optionally substituted, e.g., with one or more substituents such as halo (F, Cl, Br or I), (e.g. $CF_3$, 2-Br-ethyl, $CH_2F$, $CH_2Cl$, $CH_2CF_3$ or $CF_2CF_3$), hydroxyl (e.g. $CH_2OH$), amino (e.g. $CH_2NH_2$, $CH_2NHCH_3$ or $CH_2N(CH_3)_2$), alkylamino, arylamino, alkoxy, aryloxy, nitro, azido (e.g. $CH_2N_3$), cyano (e.g. $CH_2CN$), sulfonic acid, sulfate, phosphonic acid, phosphate, or phosphonate, either unprotected, or protected as necessary, as known to those skilled in the art, for example, as taught in Greene, et al., Protective Groups in Organic Synthesis John Wiley and Sons, Second Edition, 1991, hereby incorporated by reference.

The term "lower alkyl," as used herein, and unless otherwise specified, refers to a $C_1$ to $C_4$ saturated straight, branched, or if appropriate, a cyclic (for example, cyclopropyl) alkyl group, including both substituted and unsubstituted forms.

The term "alkylamino" or "arylamino" includes an amino group that has one or two alkyl or aryl substituents, respectively.

The term "alkaryl" or "alkylaryl" includes an alkyl group with an aryl substituent. The term aralkyl or arylalkyl includes an aryl group with an alkyl substituent.

The term "acyl" includes a carboxylic acid ester in which the non-carbonyl moiety of the ester group is selected from straight, branched, or cyclic alkyl or lower alkyl, alkoxyalkyl including methoxymethyl, aralkyl including benzyl, aryloxyalkyl such as phenoxymethyl, aryl including phenyl optionally substituted with halogen, $C_1$ to $C_4$ alkyl or $C_1$ to $C_4$ alkoxy, sulfonate esters such as alkyl or aralkyl sulphonyl including methanesulfonyl, the mono, di or triphosphate ester, trityl or monomethoxytrityl, substituted benzyl, trialkylsilyl (e.g. dimethyl-t-butylsilyl) or diphenylmethylsilyl. Aryl groups in the esters optimally comprise a phenyl group. The term "lower acyl" refers to an acyl group in which the non-carbonyl moiety is lower alkyl.

The term "subject" as used herein refers to an animal or human, such as a mammal. Mammals can include non-human mammals, including, but not limited to, pigs, sheep, goats, cows (bovine), deer, mules, horses, monkeys and other non-human primates, dogs, cats, rats, mice, rabbits or any other known mammal.

The term "nucleoside" refers to a chemical class wherein natural or endogenous nucleobases such as adenine is bound to a ribose or deoxysugar via glycosidic linkage.

The term "unnatural nucleoside" refers to a chemical class wherein modifications of nucleobase using medicinal or organic chemistry yields compounds similar in biological activities compared to naturally occurring nucleosides.

The term "storage lesion" refers to structural and functional changes to stored RBC resulting in sub-optimal clinical outcomes to transfused patients.

DETAILED DESCRIPTION

In one aspect, the present disclosure provides a blood storage and/or rejuvenating composition having triciribine, a triciribine metabolite, a triciribine prodrug, triciribine analogs, isomers, anomers and mixtures of the same. In another aspect, the present disclosure provides a platelet and/or rejuvenating composition having triciribine, a triciribine metabolite, a triciribine prodrug, triciribine analogs, isomers, anomers and mixtures of the same. In one aspect, the triciribine, triciribine metabolite, triciribine prodrug, and triciribine analog is deuterated—that is one or more hydrogen atoms is replaced with a corresponding number of deuterium atoms.

Triciribine, also known as 6-amino-4-methyl-8-(β-D-ribofuranosyl)pyrrolo [4,3,2-de]pyrimido[4,5-c-]pyridazine or (TCN), is known as an anti-cancer compound characterized by poor oral bioavailability. It has this chemical structure displayed below.

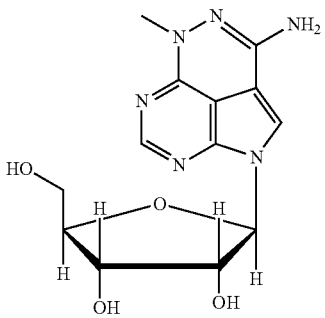

TCNP, the 5'-monophosphate analog of TCN, has the chemical structure shown below. It is also called ((2R,3S,4R,5R)-5-(3-amino-5-methyl-1,4,5,6,8-pentaazaacenaphthylen-1(5H)-yl)-3,4-dihydroxytetrahydrofuran-2-yl)methyl dihydrogen phosphate. It is a metabolite of TCN.

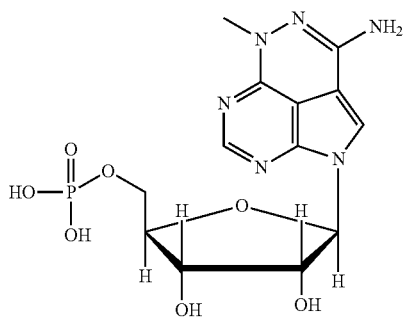

As described in Biochem. Pharmacol. 1981, 30(18), 2521-26, which is hereby incorporated by reference, TCN metabolites also include other compounds. For example, 3-amino-5-(((2R,3R,4S,5R)-3,4-dihydroxy-5-(hydroxymethyl)tetrahydro-furan-2-yl)amino)-1-methylpyrimido[4,5-c]pyridazin-4(1H)-one; ((2R,3S,4R,5R)-5-((3-amino-1-methyl-4-oxo-1,4-dihydropyrimido[4,5-c]pyridazin-5-yl)amino)-3,4-dihydroxytetrahydrofuran-2-yl)methyl dihydrogen phosphate; 3-amino-5-(((2S,3R,4S,5R)-3,4-dihydroxy-5-(hydroxymethyl) tetrahydrofuran-2-yl)amino)-1-methylpyrimido[4,5-c]pyridazin-4(1H)-one are TCN metabolites.

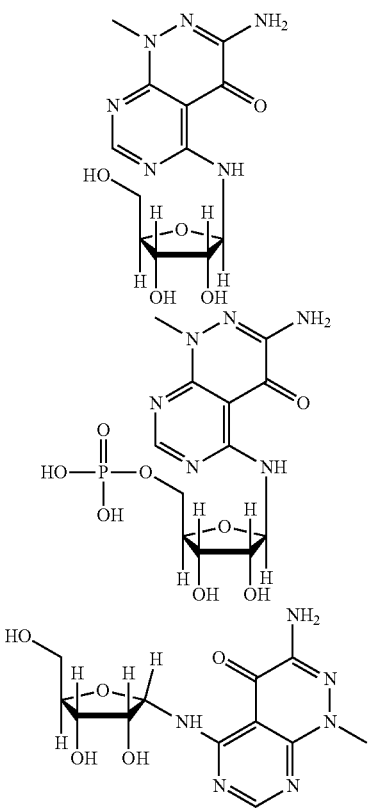

Triciribine Analogs

In one embodiment, the compounds provided herein are triciribine analogs disclosed in U.S. Patent Publication No. 2006/0247188 which is incorporated herein by reference. Such triciribine analogs include those having the structural formulas shown below:

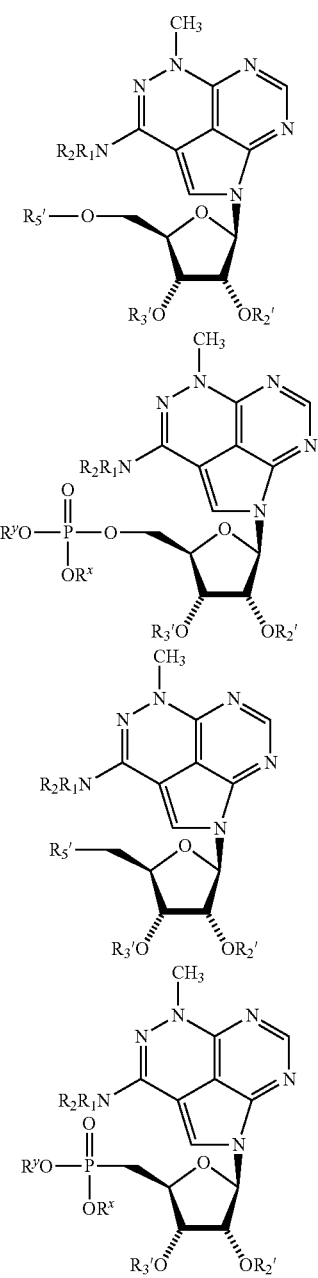

wherein each $R_2'$, $R_3'$ and $R_5'$ are independently hydrogen, optionally substituted phosphate or phosphonate (including mono-, di-, or triphosphate or a stabilized phosphate prodrug); acyl (including lower acyl); alkyl (including lower alkyl); amide, sulfonate ester including alkyl or arylalkyl; sulfonyl, including methane-sulfonyl and benzyl, wherein the phenyl group is optionally substituted with one or more substituents as for example as described in the definition of an aryl given herein; optionally substituted arylsulfonyl; a lipid, including a phospholipid; an amino acid; a carbohydrate; a peptide; or cholesterol; or other pharmaceutically acceptable leaving group that, in vivo, provides a compound wherein R2', R3' or R5' is independently H or mono-, di- or tri-phosphate; $R^X$ and $R^Y$ are independently hydrogen, optionally substituted phosphate; acyl (including lower acyl); amide, alkyl (including lower alkyl); aromatic, poly-oxyalkylene such as polyethyleneglycol, optionally substituted arylsulfonyl; a lipid, including a phospholipid; an amino acid; a carbohydrate; a peptide; or cholesterol; or other pharmaceutically acceptable leaving group. In one embodiment, the compound is administered as a 5'-phosphoether lipid or a 5'-ether lipid.

$R_1$ and $R_2$ each are independently H, optionally substituted straight chained, branched or cyclic alkyl (including lower alkyl), alkenyl, or alkynyl, CO-alkyl, CO-alkenyl, CO-alkynyl, CO-aryl or heteroaryl, CO-alkoxyalkyl, CO-aryloxyalkyl, CO-substituted aryl, sulfonyl, alkylsulfonyl, arylsulfonyl, aralkylsulfonyl.

In one embodiment, R2' and R3' are hydrogen. In another embodiment, R2' and R5' are hydrogen. In yet another embodiment, R2', R3' and R5' are hydrogen. In yet another embodiment, R2', R3', R5', RI and R2 are hydrogen.

In another embodiment, the compound has the following structure:

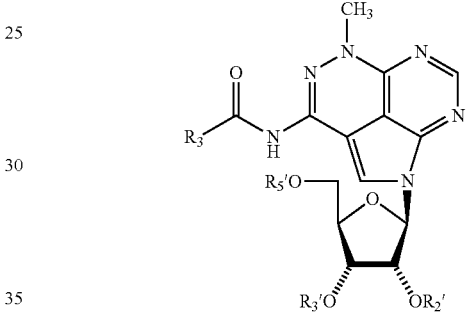

wherein $R_3$ is H, optionally substituted straight chained, branched or cyclic alkyl (including lower alkyl), alkenyl, or alkynyl, $NH_2$, $NHR^4$, $N(R^4)_2$, aryl, alkoxyalkyl, aryloxyalkyl, or substituted aryl; and each $R^4$ independently is H, acyl including lower acyl, alkyl including lower alkyl such as but not limited to methyl, ethyl, propyl and cyclopropyl, alkenyl, alkynyl, cycloalkyl, alkoxy, alkoxyalkyl, hydroxyalkyl, or aryl. In a subembodiment, R3 is a straight chained C1-11 alkyl, isopropyl, t-butyl, or phenyl.

In one embodiment, the compounds provided herein have the following structure:

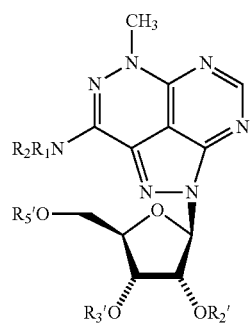

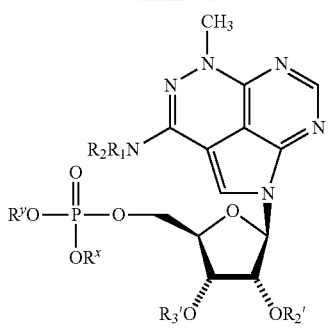

In another embodiment, the compounds provided herein have the structure:

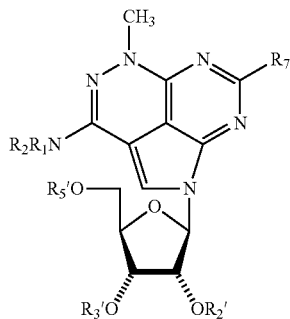

wherein $R_7$ is H, halo, alkyl (including lower alkyl), alkenyl, alkynyl, alkoxy, alkoxyalkyl, hydroxyalkyl, cycloalkyl, nitro, cyano, OH, $OR^4$, $NH_2$, $NHR^4$, $NR^4R^4$, SH, $SR^4$, $CF_3$, $CH_2OH$, $CH_2F$, $CH_2Cl$, $CH_2CF_3$, $C(Y^3)_3$, $C(Y^3)_2C(Y^3)_3$, $C(C=O)OH$, $C(C=O)OR^4$, $C(C=O)$-alkyl, $C(C=O)$-aryl, $C(C=O)$-alkoxyalkyl, $C(C=O)NH_2$, $C(C=O)NHR^4$, $C(C=O)N(R^4)_2$, or $N_3$, where each $Y^3$ is independently H or halo; and each $R^4$ independently is H, acyl including lower acyl, alkyl including lower alkyl such as but not limited to methyl, ethyl, propyl and cyclopropyl, alkenyl, alkynyl, cycloalkyl, alkoxy, alkoxyalkyl, hydroxyalkyl.

In one embodiment, $R_7$ is methyl, ethyl, phenyl, chloro or $NH_2$.

In another embodiment, the compounds provided herein have the following structure:

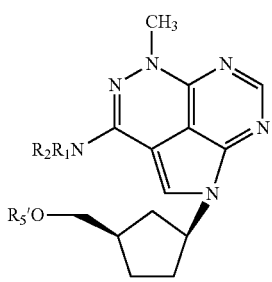

wherein $R_6$ is H, alkyl, (including lower alkyl) alkenyl, alkynyl, alkoxyalkyl, hydroxyalkyl, arylalkyl, cycloalkyl, $NH_2$, $NHR^4$, $NR^4R^4$, $CF_3$, $CH_2OH$, $CH_2F$, $CH_2C_1$, $CH_2CF_3$, $C(Y^3)_3$, $C(Y^3)_2C(Y^3)_3$, $C(C=O)OH$, $C(C=O)OR^4$, $C(C=O)$-alkyl, $C(C=O)$-aryl, $C(C=O)$-alkoxyalkyl, $C(C=O)NH_2$, $C(C=O)NHR^4$, $C(C=O)N(R^4)_2$, where each $Y^3$ is independently H or halo; and each $R^4$ independently is H, acyl including lower acyl, alkyl including lower alkyl such as but not limited to methyl, ethyl, propyl and cyclopropyl, alkenyl, alkynyl, cycloalkyl, alkoxy, alkoxyalkyl, hydroxyalkyl, or aryl.

In one embodiment, $R_6$ is ethyl, $CH_2CH_2OH$, or $CH_2$-phenyl.

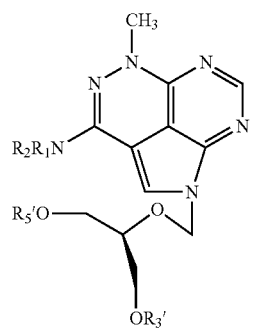

In another embodiment, the compounds provided herein have the following structure:

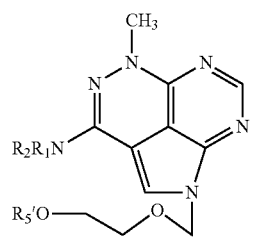

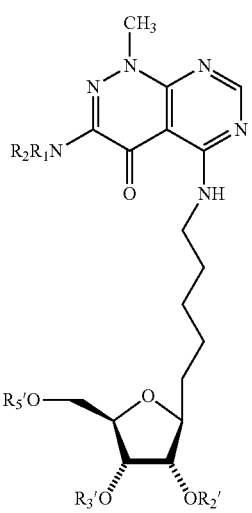

It is to be understood that the compounds disclosed herein may contain chiral centers. Such chiral centers may be of either the (R) or (S) configuration, or may be a mixture thereof. Thus, the compounds provided herein may be enantiomerically pure, or be stereoisomeric or diastereomeric mixtures. It is understood that the disclosure of a compound herein encompasses any racemic, optically active, polymorphic, or steroisomeric form, or mixtures thereof, which preferably possesses the useful properties described herein, it being well known in the art how to prepare optically active forms and how to determine activity using the standard tests described herein, or using other similar tests which are well known in the art.

Compounds described herein may be synthesized according to the methods described in U.S. Patent Publication No. 2006/0247188, which is herein incorporated by reference in its entirety.

Pharmaceutically Acceptable Salts and Prodrugs of Triciribine Analogs

In cases where compounds are sufficiently basic or acidic to form stable nontoxic acid or base salts, administration of the compound as a pharmaceutically acceptable salt may be appropriate. Pharmaceutically acceptable salts include those derived from pharmaceutically acceptable inorganic or organic bases and acids. Suitable salts include those derived from alkali metals such as potassium and sodium, alkaline earth metals such as calcium and magnesium, among numerous other acids well known in the pharmaceutical art. In particular, examples of pharmaceutically acceptable salts are organic acid addition salts formed with acids, which form a physiological acceptable anion, for example, tosylate, methanesulfonate, acetate, citrate, malonate, tartarate, succinate, benzoate, ascorbate, a-ketoglutarate, and a-glycerophosphate. Suitable inorganic salts may also be formed, including, sulfate, nitrate, bicarbonate, and carbonate salts.

Any of the nucleotides described herein can be administered as a nucleotide prodrug to increase the activity, bioavailability, stability or otherwise alter the properties of the nucleoside. A number of nucleotide prodrug ligands are known. In general, alkylation, acylation or other lipophilic modification of the mono, di or triphosphate of the nucleoside will increase the stability of the nucleotide. Examples of substituent groups that can replace one or more hydrogens on the phosphate moiety are alkyl, aryl, steroids, carbohydrates, including sugars, 1,2-diacylglycerol and alcohols.

Many are described in R. Jones and N. Bischofberger, Antiviral Research, 27 (1995) 1-17. Any of these can be used in combination with the disclosed nucleosides to achieve a desired effect.

In one embodiment, the triciribine or a related compound is provided as 5'-hydroxyl lipophilic prodrug. Nonlimiting examples of U.S. patents that disclose suitable lipophilic substituents that can be covalently incorporated into the nucleoside, preferably at the 5'-OH position of the nucleoside or lipophilic preparations, include U.S. Pat. No. 5,149,794 (Sep. 22, 1992, Yatvin, et al.); U.S. Pat. No. 5,194,654 (Mar. 16, 1993, Hostetler, et al.); U.S. Pat. No. 5,223,263 (Jun. 29, 1993, Hostetler, et al.); U.S. Pat. No. 5,256,641 (Oct. 26, 1993, Yatvin, et al.); U.S. Pat. No. 5,411,947 (May 2, 1995, Hostetler, et al.); U.S. Pat. No. 5,463,092 (Oct. 31, 1995, Hostetler, et al.); U.S. Pat. No. 5,543,389 (Aug. 6, 1996, Yatvin, et al.); U.S. Pat. No. 5,543,390 (Aug. 6, 1996, Yatvin, et al.); U.S. Pat. No. 5,543,391 (Aug. 6, 1996, Yatvin, et al.); and U.S. Pat. No. 5,554,728 (Sep. 10, 1996, Basava, et al.), all of which are incorporated herein by reference.

Foreign patent applications that disclose lipophilic substituents that can be attached to the triciribine or a related compound of the present invention, or lipophilic preparations include WO 89/02733, WO 90/00555, WO 91/16920, WO 91/18914, WO 93/00910, WO 94/26273, W0/15132, EP 0 350 287, EP 93917054.4, and WO 91/19721.

Additional nonlimiting examples of derivatives of triciribine or related compounds are those that contain substituents as described in the following publications: Ho, D. H. W. (1973) Distribution of Kinase and deaminase of 1β-D-arabinofuranosylcytosine in tissues of man and mouse. Cancer Res. 33, 2816-2820; Holy, A (1993) Isopolar phosphorous-modified nucleotide analogues. In: De Clercq (ed.), Advances in Antiviral Drug Design, Vol. I, JAI Press, pp. 179-231; Hong, C. I., Nechaev, A, and West, C. R. (1979a) Synthesis and antitumor activity of 1β-3-arabinofuranosylcytosine conjugates of cortisol and cortisone. Biochem. Biophys. Rs. Commun. 88, 1223-1229; Hong, C. I., Nechaev, A, Kirisits, A J. Buchheit, D. J. and West, C. R. (1980) Nucleoside conjugates as potential antitumor agents. 3. Synthesis and antitumor activity of I-(β-D-arabinofuranosyl) cytosine conjugates of corticosteriods and selected lipophilic alcohols. J. Med. Chem. 28, 171-177; Hostetler, K. Y, Stuhmiller, L. M., Lenting, H. B. M. van den Bosch, H. and Richman, D. D. (1990) Synthesis and antiretroviral activity of phospholipid analogs of azidothymidine and other antiviral nucleosides. J. Biol. Chem. 266, 11714-11717; Hostetler, K. Y, Korba, B. Sridhar, C., Gardener, M. (1994a) Antiviral activity of phosphatidyl-dideoxycytidine in hepatitis B-infected cells and enhanced hepatic uptake in mice. Antiviral Res. 24, 59-67; Hostetler, K. Y, Richman, D. D., Sridhar, C. N. Feigner, P. L., Feigner, J., Ricci, J., Gerdener, M. F. Selleseth, D. W. and Ellis, M. N. (1994b) Phosphatidylazidothymidine and phosphatidyi-ddC: Assessment of uptake in mouse lymphoid tissues and antiviral activities in human immunodeficiency virus-infected cells and in rauscher leukemia virus-infected mice. Antimicrobial Agents Chemother. 38, 2792-2797; Hunston, R. N., Jones, A. A., McGuigan, C., Walker, R. T., Balzarini, J., and De Clercq, E. (1984) Synthesis and biological properties of some cyclic phosphotriesters derived from 2'-deoxy-5-fluorouridine. J. Med. Chem. 27, 440-444; Ji, Y H., Moog, C., Schmitt, G, Bischoff, P. and Luu, B. (1990); Monophosphoric acid diesters of 7β-hydroxycholesterol and of pyrimidine nucleosides as potential antitumor agents; synthesis and preliminary evaluation of antitumor activity. J. Med. Chem.

33, 2264-2270; Jones, A. S., McGuigan, C., Walter, R. T., Balzarini, J. and DeCiercq, E. (1984) Synthesis, properties, and biological activity of some nucleoside cyclic phosphoramidates. J. Chem. Soc. Perkin Trans. I, 1471-1474; Juodka, B. A and Smart, J. (1974) Synthesis of diribonucleoside phospho (P→N) amino acid derivatives. Coll. Czech. Chem. Comm. 39, 363-968; Kataoka, S., Imai, J., Yamaji, N., Kato, M., Saito, M., Kawada, T. and Imai, S. (1989) Alkylated cAMP derivatives; selective synthesis and biological activities. Nucleic Acids Res. Sym. Ser., 21, 1-2; Kataoka, S., Uchida, R. and Yamaji, N. (1991) A convenient synthesis of adenosine 3',5'cyclic phosphate (cAMP) benzyl and methyl triesters. Heterocycles 32, 1351-1356; Kinchington, D., Harvey, J. J., O'Connor, T. J., Jones, B. C. N. M., Devine, K. G., Taylor-Robinson, D., Jeffries, D. J. and McGuigan, C. (1992) Comparison of antiviral effects of zidovudine phosphoramidate and phosphorodiamidate derivatives against HIV and ULV in vitro. Antiviral Chem. Chemother. 3,107-112; Kodama, K., Morozumi, M., Saitoh, K. 1., Kuninaka, H., Yoshino, H. and Saneyoshi, M. (1989) Antitumor activity and pharmacology of I-β-D-arabinofuranosylcytosine-5'-stearylphosphate; an orally active derivative of I-β-D-arabinofuranosylcytosine. Jpn. J. Cancer Res. 80, 679-685; Korty, M. and Engels, J. (1979) The effects of adenosine- and guanosine 3',5'-phosphoric and acid benzyl esters on guinea-pig ventricular myocardium. NaunynSchmiedeberg'sArch. Pharmacol. 310, 103-111; Kumar, A., Goe, P. L., Jones, A. S. Walker, R. T. Balzarini, J. and De Clercq, E. (1990) Synthesis and biological evaluation of some cyclic phosphoramidate nucleoside derivatives. J. Med. Chem. 33, 2368-2375; LeBec, C., and Huynhdinh, T. (1991) Synthesis of lipophilic phosphate triester derivatives of 5-fluorouridine and arabinocytidine as anticancer prodrugs. Tetrahedron Lett. 32, 6553-6556; Lichtenstein, J., Barner, H. D. and Cohen S. S. (1960) The metabolism of exogenously supplied nucleotides by *Escherichia coli*., J. Biol. Chem. 235, 457-465; Lucthy, J., Von Daeniken, A, Friederich, J. Manthey, B., Zweifel, J., Schlatter, C. and Benn, M. H. (1981) Synthesis and toxicological properties of three naturally occurring cyanoepithioalkanes. Mitt. Geg. Lebensmittelunters. Hyg. 72, 131-133 (Chem. Abstr. 95, 127093); McGuigan, C., Tollerfield, S. M. and Riley, P. A (1989) Synthesis and biological evaluation of some phosphate triester derivatives of the anti-viral drug Ara. Nucleic Acids Res. 17, 6065-6075; McGuigan, C., Devine, K. G., O'Connor, T. J., Galpin, S. A, Jeffries, D. J. and Kinchington, D. (1990a) Synthesis and evaluation of some novel phosphoramidate derivatives of 3'-azido-3'-deoxythymidine (AZT) as anti-HIV compounds. Antiviral Chem. Chemother. 1, 107-113; McGuigan, C., O'Connor, T. J., Nicholls, S. R. Nickson, C. and Kinchington, D. (1990b) Synthesis and anti-HIV activity of some novel substituted dialkyl phosphate derivatives of AZT and ddCyd. Antiviral Chem. Chemother. 1, 355-360; McGuigan, C., Nicholls, S. R., O'Connor, T. J., and Kinchington, D. (1990c) Synthesis of some novel dialkyl phosphate derivative of 3'-modified nucleosides as potential anti-AIDS drugs. Antiviral Chem. Chemother. 1, 25-33; McGuigan, C., Devine, K. G., O'Connor, T. J., and Kinchington, D. (1991) Synthesis and anti-HIV activity of some haloalkylphosphoramidate derivatives of 3'-azido-3'deoxythylmidine (AZT); potent activity of the trichloroethyl methoxyalaninyl compound. Antiviral Res. 15, 255-263; McGuigan, C., Pathirana, R. N., Mahmood, N., Devine, K. G. and Hay, A J. (1992) Aryl phosphate derivatives of AZT retain activity against HIV1 in cell lines which are resistant to the action of AZT. Antiviral Res. 17, 311-321; McGuigan, C., Pathirana, R. N., Choi, S. M., Kinchington, D. and O'Connor, T. J. (1993a) Phosphoramidate derivatives of AZT as inhibitors of HIV; studies on the caroxyl terminus. Antiviral Chem. Chemother. 4, 97-101; McGuigan, C., Pathirana, R. N., Balzarini, J. and De Clercq, E. (1993b) Intracellular delivery of bioactive AZT nucleotides by aryl phosphate derivatives of AZT. J. Med. Chem. 36, 1048-1052; each of which is incorporated herein by reference in their entirety.

Additional examples of prodrugs that can be used are those described in the following patents and patent applications: U.S. Pat. Nos. 5,614,548, 5,512,671, 5,770,584, 5,962,437, 5,223,263, 5,817,638, 6,252,060, 6,448,392, 5,411,947, 5,744,592, 5,484,809, 5,827,831, 5,696,277, 6,022,029, 5,780,617, 5,194,654, 5,463,092, 5,744,461, 4,444,766, 4,562,179, 4,599,205, 4,493,832, 4,221,732, 5,116,992, 6,429,227, 5,149,794, 5,703,063, 5,888,990, 4,810,697, 5,512,671, 6,030,960, 2004/0259845, U.S. Pat. No. 6,670,341, 2004/0161398, 2002/082242, U.S. Pat. No. 5,512,671, 2002/0082242, and/or PCT Publication Nos. WO 90/11079, WO 96/39197, and/or WO 93/08807, each of which is incorporated by reference in their entirety.

Prodrugs of triciribine and its TCNP metabolite are disclosed in U.S. Patent Publication No. 2010/0093609 which is incorporated herein by reference. Such prodrugs include those having the structural formula:

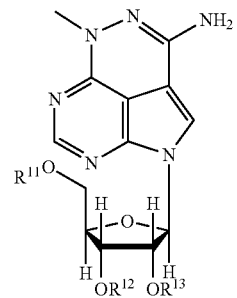

where $R_{11}$, $R_{12}$, and $R_{13}$ are each independently H, or selected from the group consisting of: an amino acid, a dipeptide, a tripeptide, and

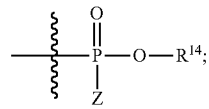

where Z and at least one of $R_{11}$, $R_{12}$ and $R_{13}$ is an amino acid, a dipeptide or a tripeptide; where $R_{14}$ is aliphatic, aryl, or heteroaryl; or a salt or hydrate thereof.

Optionally, $R_{11}$ is selected from the group consisting of: an amino acid, a dipeptide a tripeptide, and

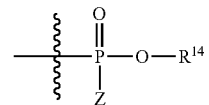

where $R_{12}$ and $R_{13}$ are each independently H, an amino acid, a dipeptide, a tripeptide or

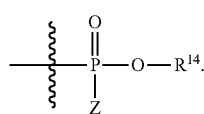

In another option, at least one of $R_{11}$, $R_{12}$, $R_{13}$, and

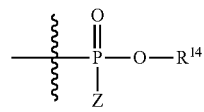

is a substrate for a transporter.

In another embodiment, $R_{11}$ is an amino acid or

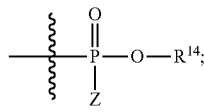

$R_{12}$ and $R_{13}$ are both H; and Z is an amino acid.

Naturally-occurring or non-naturally occurring amino acids can be used to prepare the prodrug forms of TCN and TCNP. In particular, standard amino acids suitable as a prodrug moiety include valine, leucine, isoleucine, methionine, phenylalanine, asparagine, glutamic acid, glutamine, histidine, lysine, arginine, aspartic acid, glycine, alanine, serine, threonine, tyrosine, tryptophan, cysteine and proline. In some embodiments, L-amino acids are used. In some embodiments, an included amino acid is an α-, β-, or γ-amino acid. In some embodiments, naturally-occurring, non-standard amino acids can be utilized in the compositions and methods of the invention. For example, in addition to the standard naturally occurring amino acids commonly found in proteins, naturally occurring amino acids also illustratively include 4-hydroxyproline, γ-carboxyglutamic acid, selenocysteine, desmosine, 6-N-methyllysine, 3-methylhistidine, O-phosphoserine, 5-hydroxylysine, ε-N-acetyllysine, Ω-N-methylarginine, N-acetylserine, γ-aminobutyric acid, citrulline, ornithine, azaserine, homocysteine, β-cyanoalanine and S-adenosylmethionine. Non-naturally occurring amino acids include phenyl glycine, meta-tyrosine, para-amino phenylalanine, 3-(3-pyridyl)-L-alanine, 4-(trifluoromethyl)-D-phenylalanine, and the like.

In one embodiment, the amino acid covalently coupled to the pharmaceutical species is a non-polar amino acid such as valine, phenylalanine, leucine, isoleucine, glycine, alanine and methionine.

In one embodiment, more than one amino acid is covalently coupled to the pharmaceutical species. For example, a first and second amino acid are each covalently coupled to separate sites on the pharmaceutical species. In another example, a dipeptide is covalently coupled to the pharmaceutical species. In another embodiment, a tripeptide is covalently coupled to the pharmaceutical species.

In some embodiments, at least one of $R_{11}$, $R_{12}$, and $R_{13}$ is: -D-isoleucyl; -L-isoleucyl; -D-valy; -L-valyl; -glycyl; -D-phenylalanyl; -L-phenylalanyl; -D-leucyl; -L-leucyl; -L-aspartyl; -D-α-aspartyl; -L-α-aspartyl; -D-β-aspartyl; -L-β-aspartyl; and -L-prolyl; -D-isoleucyl phosphoramidate; -L-isoleucyl phosphoramidate; -D-valyl phosphoramidate; -L-valyl phosphoramidate; -glycyl phosphoramidate; -D-phenylalanyl phosphoramidate; -L-phenylalanyl phosphoramidate; -D-leucyl phosphoramidate TCN; 5'-O-L-leucyl phosphoramidate TCN; 5'-O-L-aspartyl phosphoramidate; -D-α-aspartyl phosphoramidate; -L-α-aspartyl phosphoramidate; D-β-aspartyl phosphoramidate; -L-β-aspartyl phosphoramidate; or -L-prolyl phosphoramidate.

TCN prodrugs, therefore, include the following: 5'-O-D-isoleucyl TCN; 5'-O-L-isoleucyl TCN; 5'-O-D-valyl TCN; 5'-O-L-valyl TCN; 5'-O-glycyl TCN; phenylalanyl TCN; 5'-O-L-phenylalanyl TCN; TCN; TCN; 5'-O-L-aspartyl TCN; 5'-O-D-alpha-aspartyl TCN; 5'-O-L-alpha-aspartyl TCN; 5'-O-D-beta-aspartyl TCN; 5'-O-L-beta-aspartyl TCN.

TCNP prodrugs, therefore include the following: 5'-O-L-prolyl TCN 5-O-D-isoleucyl phosphoramidate TCN; 5'-O-L-isoleucyl phosphoramidate TCN; 5'-O-D-valyl phosphoramidate TCN; 5'-O-L-valyl phosphoramidate TCN; 5'-O-glycyl phosphoramidate TCN; 5'-O-D-phenylalanyl phosphoramidate TCN; 5'-O-L-phenylalanyl phosphoramidate TCN; phosphoramidate TCN; phosphoramidate TCN; 5'-O-L-aspartyl phosphoramidate TCN; 5'-O-D-alpha-aspartyl phosphoramidate TCN; 5'-O-L-α-aspartyl phosphoramidate TCN; 5-O-D-β-aspartyl phosphoramidate TCN; 5-O-L-β-aspartyl phosphoramidate TCN; and 5'-O-L-prolyl phosphoramidate TCN.

Optionally, the composition can further include sodium pyruvate and/or inorganic phosphate. In certain embodiments the composition is an aqueous solution. In preferred embodiments, the composition is an aqueous composition having a pH of 6 to 8.5.

In another embodiment, the blood storage, platelet and/or rejuvenating composition includes 0.01 uM to 10 mM of triciribine, a triciribine metabolite, a triciribine prodrug, deuterated triciribine analog and mixtures of the same.

Optionally, the composition can further include additives or adjuvants such as sodium chloride, sodium bicarbonate, sodium phosphate dibasic, monosodium phosphate (i.e., sodium dihydrogen phosphate), citric acid, sodium citrate, sodium pyruvate, arginine, adenine, guanosine, inosine, dextrose, ribose, and mannitol. For example, D-ribose at a concentration of, for example, 75 to 1500 mM. Optionally, the composition can further include sodium pyruvate at a concentration of, for example, 75 to 1500 mM. Optionally, the composition can further include an inorganic phosphate at a concentration of, for example, 75 to 1500 mM. Optionally, the composition can further include L-arginine at a concentration of, for example, 75 to 1500 mM. Optionally, the composition can further include inosine at a concentration of, for example, 75 to 1500 mM. When used to store and/or rejuvenate blood or platelets or both, the composition is typically diluted approximately 30-fold to provide a final concentration of 2.5 to 50 mM guanosine; and optionally 2.5 to 50 mM D-ribose, 2.5 to 50 mM sodium pyruvate, 2.5 to 50 mM inorganic phosphate, 2.5 to 50 mM L-arginine, and/or 2.5 to 50 mM inosine. Examples of well-known additive solutions that can optionally be used include SAGM, AS-1 (Adsol®; Fenwal Inc. Three Corporate Drive Lake Zurich, Ill. 60047 USA), AS-3 (Nutricel® Medsep Corporation, A Subsidiary of Pall Corp., Covina, Calif. 91722 USA), AS-5 (Optisol® Terumo Corporation Tokyo, Japan), AS-7 (SOLX® Hemerus Medical, LLC 5000 Township Parkway St. Paul, Minn. 55110 USA) MAP, and PAGGSM, as described generally in Blood Transfus. 2012, 10 (Suppl. 2), s7-11, which is hereby incorporated by reference.

The compositions described herein can be used, for example, in a method of storing blood or platelets or both.

In certain embodiments, the method includes contacting RBCs with a blood storage and/or rejuvenating composition as described herein. In certain embodiments, the method includes contacting platelets with a platelet storage and/or rejuvenating composition as described herein.

Alternatively, or in addition to, the compositions described herein can be used, for example, in a method of rejuvenating blood or platelets or both. In certain embodiments, the method includes contacting RBCs or platelets or both with a blood storage and/or rejuvenating composition as described herein.

In some embodiments, the method of rejuvenating blood includes: providing RBCs (e.g., packed RBCs or in whole blood) having a 2,3-DPG value lower than the value for freshly drawn blood; and mixing the RBCs with a blood storage and/or rejuvenating composition under conditions effective to increase the 2,3-DPG value, wherein the blood storage and/or rejuvenating composition includes guanosine. In some embodiments, conditions effective to increase the 2,3-DPG value include incubating the cells in the blood storage and/or rejuvenating composition at a temperature of 4° C. to 37° C., and in some embodiments at a temperature of room temperature. In certain embodiments, conditions effective to increase the 2,3-DPG value include incubating the red blood cells with the blood storage and/or rejuvenating composition for a time of at least 10 minutes, for example about 10 minutes to 48 hours; from about 10 minutes to about 4 hours; from about 30 minutes to 2 about hours. Exemplary conditions effective to increase the 2,3-DPG value include incubating the cells in the blood storage and/or rejuvenating composition at 37° C. for about 10 minutes to 4 hours. Other exemplary conditions effective to increase the 2,3-DPG value include incubating the red blood cells with the blood storage and/or rejuvenating composition at room temperature for about 10 minutes to 4 hours. In some embodiments, the blood storage and/or rejuvenating composition includes one or more of the blood storage and/or rejuvenating compositions described herein.

TCNP was recently demonstrated to be active metabolite of TCN binding to pleckstrin homology (PH) domain of Akt ($K_D$=690 nM). Spectrin is one of the key membrane proteins of RBC for maintaining RBC shape and mechanical properties. Spectrin has been shown to have PH domain and phosphorylation/dephosphorylation of spectrin modulates membrane mechanical stability of intact RBC membranes. Without wishing to be bound to any particular theory, it is believed that an inverse correlation between phosphorylation of Spectrin and mechanical stability of RBC membranes demonstrates that inhibition of spectrin phosphorylation could be a novel mechanism for maintaining RBC membrane integrity during storage to reduce or eliminate storage lesions. TCNP is envisioned to be an inhibitor of spectrin phosphorylation by binding to PH domain of spectrin similar to its demonstrated activity in inhibition Akt phosphorylation by binding to the PH domain of this protein.

Calcium is an important regulator of cellular activity, and RBC free calcium levels are maintained at less than 60 nM. Plasma calcium concentrations can be as high as 1.8 mM. Influx of calcium has been associated with externalization of a phosphatidylserine, a phospholipid limited to inner leaflets of membranes in healthy cells. Externalization of phosphatidylserine is referred to as an "eat me" signal, and such RBCs are routed for phagocytosis or other cellular destruction. Without wishing to be bound to any particular theory, it is believed that TCN is capable of being metabolized to TCNP in RBC and reduce calcium mediated externalization of phyosphatidylserine thereby reducing eryptosis and RBC hemolysis.

Eryptosis is a common feature of a number disorders such as sickle cell, beta thalassemia, Wilson's disease, paroxysmal nocturnal hemoglobinuria, diabetes, renal insufficiency, sepsis, hemolytic uremic syndrome, hereditary spherocytosis, malaria, sepsis, mycoplasma infection, iron deficiency, G6PD deficiency, myelodysplastic syndrome and phosphate depletion. Transfusion of TCN/TCNP containing RBC in patients with these conditions is envisioned to alleviate eryptosis and hemolysis thereby contributing to superior clinical outcomes and quality of life for patients suffering from such disorders.

Calcium binds to calmodulin (CaM), and this complex and a downstream interaction of this complex to RBC membrane proteins thereby destabilizing the RBC membrane. TCN/TCNP is envisioned to antagonize binding of Ca-CaM to membrane protein complexes and, therefore, reduce RBC Eryptosis or hemolysis.

The present disclosure invention is illustrated by the following examples. It is to be understood that the particular examples, materials, amounts, and procedures are to be interpreted broadly in accordance with the scope and spirit of the invention as set forth herein.

EXAMPLES

Blood (RBC) Partitioning

In order to evaluate accumulation of TCN and TCNP in RBC and to contrast this with accumulation in plasma, partitioning studies were conducted as noted below. In this example, blood refers to RBC.

Partitioning of TCN and TCNP was evaluated in rat blood at 0, 0.25 and 1 hour time period post drug incubation. Rat blood was collected using established procedures. Drug stocks were prepared at 2500 µM for TCN in methanol and 2500 µM for TCNP in 10 mM ammonium acetate pH 7.4. A stock of AMP (Adenosine 5'-monophosphate) was also prepared at 10 mg/mL in ultrapure water. From these stocks a set of samples were prepared at 25 µM for TCN and 25 µM for TCNP in mobile phase (95:5 0.1% formic acid in water: acetonitrile), and a set of samples were prepared at 25 µM for TCN or TCNP in rat whole blood. The mobile phase samples were used to calculate the % remaining for the samples prepared in rat whole blood. At each time point, an 800 µL aliquot of the whole blood sample was removed, combined with 8 µL AMP stock to result in 100 µg/ml AMP, and inverted to mix. Immediately following addition of the AMP, a 500 µL portion of this aliquot was spun to plasma by centrifuging the sample for 10 minutes at 7,000 rpm, and 200 µL of plasma was then treated with 200 µL of acetonitrile, vortexed, and then centrifuged for 10 minutes at 10,000 g. Separately, a 200 µL portion of the whole blood combined with AMP was treated with 200 µL acetonitrile, vortexed, and then centrifuged at 10,000 g. After both the plasma and whole blood samples were treated with acetonitrile and centrifuged, the supernatant was collected and placed in a HPLC vial for injection.

Representative data from one set of studies is shown in Table 1. Results from these studies indicate the propensity of TCNP to accumulate in blood as a function of time whereas the concentration of TCN and TCNP in plasma decreases as a function of time. Accumulation of TCNP in blood after 1 hour was greater than 20-fold relative to accumulation of TCN in blood or plasma regardless of whether the starting drug used was TCN or TCNP. TCNP concentrations in human RBC exceed 50 μM with prolonged retention (half-life of 89 hours) after intravenous administration with a similar 20-fold difference in the accumulation of TCNP in blood relative to TCN in plasma. Rat blood may be a suitable surrogate for use of in vitro studies to quantify uptake of TCN and its metabolites.

TABLE 1

Rat Blood and Plasma partitioning of TCN and TCNP expressed as % drug relative to mobile phase

| Min | TCN Blood | TCN Plasma | TCNP Blood | TCNP Plasma |
|---|---|---|---|---|
| | Drug: 25 μM TCN in blood | | | |
| 0 | 57.4% | 32.8% | 6.7% | 0.6% |
| 15 | 1.8% | 5.7% | 24.8% | 3.0% |
| 60 | 0.9% | 2.5% | 19.6% | 2.3% |
| | Drug: 25 μM TCNP in blood | | | |
| 0 | 5.4% | 12.5% | 41.7% | 48.9% |
| 15 | 2.0% | 4.6% | 33.1% | 6.7% |
| 60 | 1.1% | 1.7% | 28.3% | 2.7% | mobile phase: 25 μM TCN
mobile phase: 25 μM TCNP

Mechanical Fragility

RBC Mechanical Fragility (MF) is a potential measure of RBC health or viability, so some preliminary data was collaboratively generated on the composition's effect of RBC mechanical fragility.

RBC Fragility Test

Samples of the pRBC were sterilely obtained from the units at 23 days past collection. These samples were diluted to total Hb ($Hb^T$) concentration of 1.6-1.7 g/dl, corresponding to about 4% hematocrit, with AS-3 storage buffer (with and without TCN), pH 5.75 containing either 0 or 40 g/L albumin (Sigma). A stock solution of TCN was prepared in AS-3 storage buffer at a concentration of 1 mg/ml from an initial stock solution of TCN in DMSO at 10 mg/ml. In order to determine the effect of concentration on RBC fragility, samples were tested at 0 (buffer+DMSO) and 100 uM of TCN in final diluted samples. The diluted sample was gently mixed for 30 minutes to allow for RBC uptake at room temperature and aliquotted into 2 ml low-retention centrifuge tubes at 330 μl per tube in triplicates (i.e., n=3) and stored for 1, 11, and 21 days at 4° C. Mechanical stress was applied to RBC samples with the use of a TissueLyser LT (Qiagen) bead mill (at an oscillation frequency of 50 Hz) in the presence of one 7 mm diameter stainless steel ball for a predetermined duration. Samples from each RBC unit were subjected to such stress at 10 different durations (1, 5 and 10 minutes) to ensure a wide range of achieved hemolysis levels. The sample holder of the TissueLyser was modified to allow air cooling while in operation, which resulted in sample temperature stabilization within 2 degrees of the 22° C. start temperature. Un-lysed cells were precipitated by centrifuging the samples for 5 minutes at 1,300 RPM. Aliquots of supernatant was collected and used for spectral analysis.

Hemolysis Assessment

Hemolysis (Hem), both present in untreated sample and induced by the bead mill, was determined based on the difference in absorbance at 576 nm, a wavelength of oxygenated Hb maximum, and absorbance at 700 nm. It was expressed as a fraction of free hemoglobin (HBF) relative to total hemoglobin concentration ($Hb^T$) according to Formula 1 (below) with the correction for sample hematocrit as detailed by Sowemino-Coker {Sowemimo-Coker, 2002 #26678} (see Formula 2 below). Total hemoglobin concentration for each diluted RBC sample was determined by subjecting a small (30-40 μL) aliquot to repeated (5×) rapid freeze-thaw using liquid nitrogen. In control experiments, such treatment was shown to fully lyse RBC.

$$Hem = \frac{Hb^F_{576} - Hb^F_{700}}{Hb^T_{576} - Hb^T_{700}}$$ Formula 1

$$Hem_{corr} = Hem * (1 - \text{Hematocrit})$$ Formula 2

For auto-hemolysis (hemolysis prior to the application of mechanical stress) determination, small (20 μl) samples of undiluted segments' contents were centrifuged for 5 minutes at 1,300 rpm, supernatants were collected, and hemoglobin content was measured using a spectrophotometer. Percent lysis ($Hem_{zero}$) was calculated as described above.

Total Hemoglobin concentrations in diluted and undiluted samples had been independently measured using a Hemoglobin B system from HemoCue. Spectroscopic measurements were performed with NanoDrop N100 spectrophotometer (NanoDrop).

RBC fragility profiles are defined as the incremental (amount exceeding auto-hemolysis values) hemolysis for applied variable stress durations. Profiles were described by the parameters representing amount of hemolysis achieved as a result of small ($Hem_1$; 1 minute), medium ($Hem_5$; 5 minutes) and large ($Hem_{10}$; 10 minutes) stress durations, corresponding to small, medium and large total applied stress magnitude. Fragility parameters at particular stress duration were obtained from best fit second-order polynomial regression to the experimental data. For curves exhibiting significant deviations from a simple polynomial, raw data was subdivided into low and high hemolysis sub-sets and the fits were obtained independently for each subset of the data.

Representative data from one set of studies depicted as the difference [RBC+DMSO]−[RBC+DMSO+Drug] in hemolysis at different time-points in applied external stress duration (1 min, 5 min and 10 min—marked as H1, H5 and H10 correspondingly) is shown in FIG. 1. The largest difference is associated with H5 parameter with the changes in H1 and H10 significantly smaller. However all changes are in the same direction supporting the hypothesis that treatment with TCN protect RBC from storage-induced increase in mechanical fragility.

Hemolysis and Microparticle Measurement and Drug Analysis

C57BL/6J male and female mice (Jackson Labs, ME) were acclimatized for 2-3 days and ~1 ml of blood was collected using cardiac puncture and CPDA as the anti-coagulant. Collected blood was centrifuged at 2000×g for 5 minutes at 4° C. In sterile conditions, under the laminar flow hood at room temperature, the plasma and buffy coat was gently removed using a pipette. Approximately 350 to 400 μl sample of the remaining red blood cells was removed and placed into a separate sterile Eppendorf tube. Each sample was brought to a hematocrit of 60% by adding the required amount of either Adsol (control) or TCN containing Adsol (treatments). TCN stock solution of 0.5 mM was prepared in Adsol and diluted appropriately to yield a final concentration of 5 and 50 μM as treatment groups. Control and treatment groups were tested in triplicate (n=3). Samples were gently drawn into a syringe ensuring no headspace and were stored at 4° C. Aliquots were collected over the course of two weeks typically at Day 0, 2, 5, 10 or 12 and assayed for hemoglobin content to measure hemolysis and number of microparticles. For the hemolysis assay, the samples were pelleted and cell-free heme was measured in the supernatant using spectroscopy at 450-700 nm. For the measurement of microparticles, RBC were incubated with anti-glycophorin A FITC conjugated antibody TER-119 and assayed using FACS (Becton Dickinson, Franklin Lakes, N.J.) and events acquired using CellQuest software. Approximately 100,000 events were collected per measurement and all analysis completed using FlowJo software (Tree Star Inc., Ashland, Oreg.). Intracellular levels of TCN and TCNP from a satellite group of 50 μM was quantitated using a LC/MS/MS method. Briefly, 50 to 100 μl of samples were subjected to protein precipitation using 1:2 or 1:3 volumes of acetonitrile, centrifuged at 15000 rpm and supernatant transferred to HPLC vials and injected on the mass spectrometer to determine peak areas of TCN and TCNP as a function of initial concentration and duration of storage.

Figure 2:
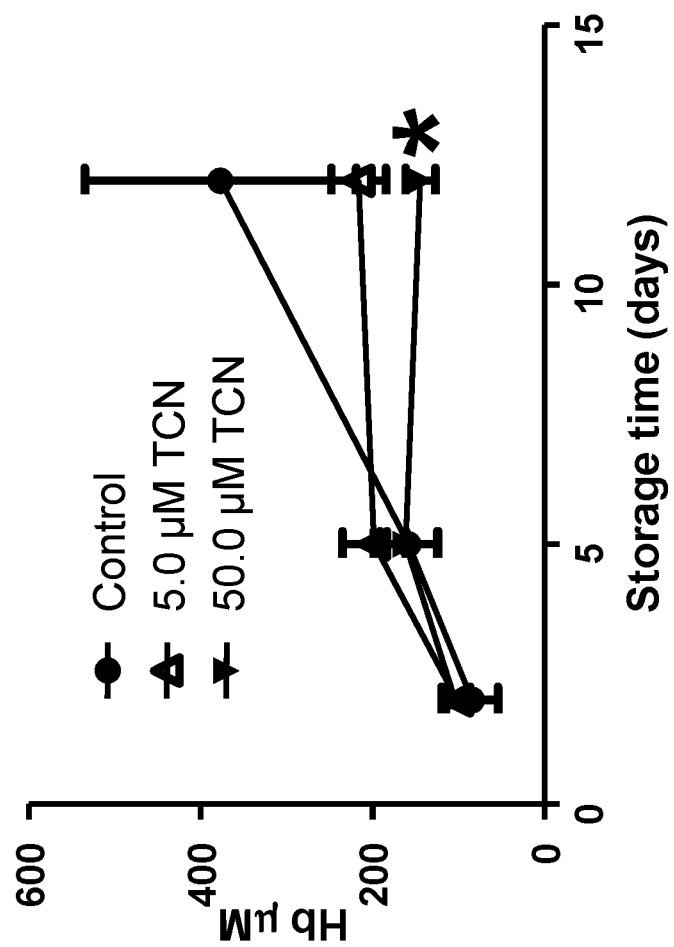
FIG. 2 shows the effect of TCN over storage time on hemolysis of mouse RBC.
Figure 3:
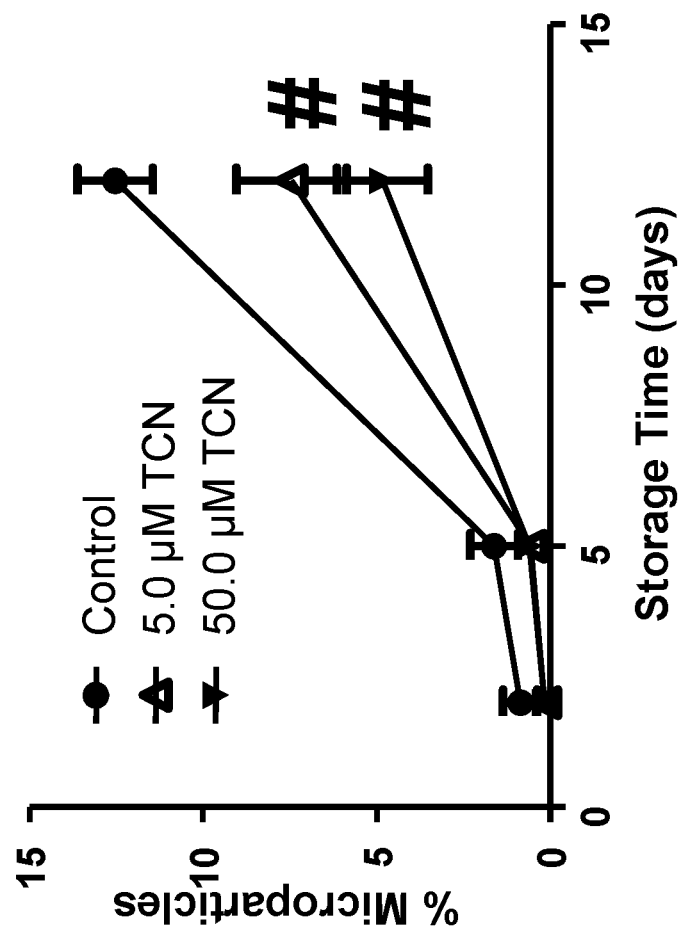
FIG. 3 shows the effect of TCN over storage time on microparticle formation in mouse RBC.

As shown in FIG. 2, TCN reduces hemolysis in stored mouse RBC at day 12 by 43% and 62% at 5 and 50 μM relative to control treatments at day 12. The effects on hemolysis were statistically significant as shown by p<0.05 for 50 μM vs. control by 2-way ANOVA with Tukey post test. In addition, as shown in FIG. 3, TCN reduced the formation of microparticles at day 12 by 40 and 62% at 5 and 50 μM relative to control treatments respectively in mouse RBC. The effects on microparticle formation were statistically significant as shown by p<0.01 for 5 μM and 50 μM vs. control by 2-way ANOVA with Tukey post test. Since integrity of the RBC membrane is critical for retention of structure and function of transfused RBC, hemolysis and microparticles have been established as markers for derangement of stored RBC. Drug treatment significantly reduces both of these markers showing the use of TCN as a novel storage additive for preserving blood to improve post-transfusion outcomes. Table 2 shows drug levels quantitated in the satellite group samples as a function of storage in mouse RBC and indicate uptake of TCN and metabolism to its active phosphate analog (TCNP). Satellite group tested was at 50 μM, n=4. In addition, compared to Day 1, TCNP levels increased 293 and 518% on Day 5 and 11 respectively, in direct correlation with the reduction of hemolysis and microparticles during this period providing evidence of pharmacological drug action.

TABLE 2

Uptake of TCN (50 uM) in mouse red blood cells and metabolism to TCNP. Drug levels is expressed as peak areas from chromatograms.

| | Day | | | | | |
|---|---|---|---|---|---|---|
| | 0 | | 5 | | 11 | |
| | TCN | TCNP | TCN | TCNP | TCN | TCNP |
| Satellite group 1 | 1739 | 122 | 4127 | 489 | 2342 | 601 |
| Satellite group 2 | 895 | 86 | 1921 | 399 | 2526 | 550 |
| Satellite group 3 | 1126 | 137 | 3049 | 483 | 2010 | 676 |
| Satellite group 4 | 930 | 89 | 2069 | 335 | 2040 | 858 |
| Average | 1172.5 | 108.5 | 2791.5 | 426.5[a] | 2229.5 | 671.25[a] |
| Std Dev | 391.11 | 25.04 | 1021.38 | 73.55 | 248.1 | 134.83 |
| % CV | 33.4 | 23.1 | 36.6 | 17.2 | 11.1 | 20.1 |
| % Difference from Day 0 | NA | NA | 138.1 | 293.1 | 90.1 | 518.7 |

[a]p < 0.05 compared to day 1 by one-way ANOVA with Tukey post test.

For human samples, blood from one consenting donor was collected using established procedures and under informed consent. Collected RBC was leukoreduced using Sepacell Flex excel filters prior to conducting studies for measurement of hemolysis and microparticles as per the procedure described above for mice samples. Leukoreduced blood sample was divided appropriately to yield n=4 replicates for control and treatment group.

Figure 4:
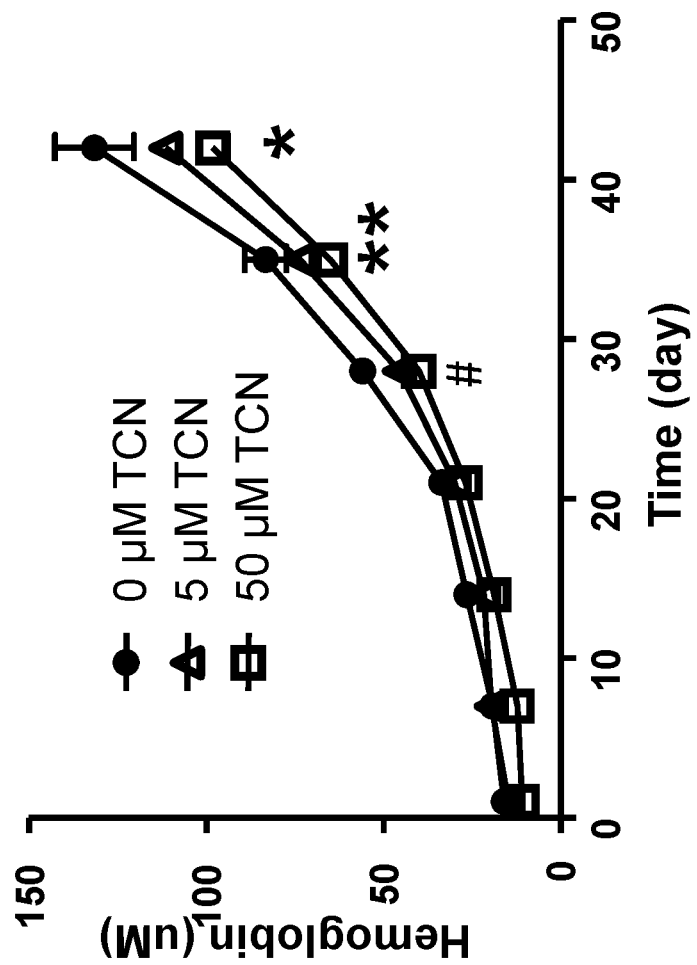
FIG. 4 shows the effect of TCN over storage time on hemolysis of human RBC.

Similar to the effect of TCN in mouse RBC samples, as shown in FIG. 4, TCN at 5 and 50 μM, reduced hemolysis by greater than 25% at Days 28 and 35 compared to control. The results at days 28 and 35 were statistically significant as shown by p<0.05 and 0.01 at 50 μM respectively vs. control by 2-way ANOVA with Tukey post test. At day 42, 5 and 50 μM TCN reduced hemolysis by 15% and 25% respectively, compared to control (p<0.001 at both concentrations vs. control by 2-way ANOVA with Tukey post test).

The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:
1. A composition comprising:
a compound selected from the group consisting of:
((2R,3S,4R,5R)-5-(3-amino-5-methyl-1,4,5,6,8-pentaazaacenaphthylen-1(5H)-y)-3,4-dihydroxytetrahydrofuran-2-yl)methyl dihydrogen phosphate;
3-amino-5-(((2R,3R,4S,5R)-3,4-dihydroxy-5-(hydroxymethyl)tetrahydro-furan-2-yl)amino)-1-methylpyrimido[4,5-c]pyridazin-4(1H)-one; and
((2R,3S,4R,5R)-5-((3-amino-1-methyl-4-oxo-1,4-dihydropyrimido[4,5-c]pyridazin-5-yl)amino)-3,4-dihydroxytetrahydrofuran-2-yl)methyl dihydrogen phosphate; and
donated blood or a component thereof.
2. The composition of claim 1, further comprising an anticoagulant.
3. The composition of claim 1, wherein the component of donated blood is suspended in at least one of a buffer and an additive solution.
4. The composition of claim 1, wherein the component of donated blood comprises platelets.
5. The composition of claim 1, wherein the component of donated blood comprises red blood cells.
6. The composition of claim 5, wherein the red blood cells are packed blood cells.
7. The composition of claim 1, wherein the component of donated blood comprises plasma.
8. A composition comprising:
donated plasma, and
a compound selected from the group consisting of:
((2R,3S,4R,5R)-5-(3-amino-5-methyl-1,4,6,8-pentaazaacenaphthylen-1(5H)-yl)-3,4-dihydroxtetrahydrofuran-2-yl)methyl dihydrogen phosphate;
3-amino-5-(((2R,3R,4S,5R)-3,4-dihydroxy-5-(hydroxymethyl)tetrahydro-furan-2-yl)amino)-1-methylpyrimido[4,5-c]pyridazin-4(1 H)-one; and
((2R,3S,4R,5R)-5-((3-amino-1-methyl-4-oxo-1,4-dihydropyrimido[4,5-c]pyridazin-5-yl)amino)-3,4-dihydroxytetrahydrofuran-2-yl)methyl dihydrogen phosphate.
9. The composition of claim 8, further comprising an anticoagulant.
10. The composition of claim 8, further comprising donated platelets.
11. The composition of claim 10, wherein the donated platelets are suspended in at least one of a buffer, an additive solution, and the donated plasma.

12. A composition comprising:
   donated red blood cells, and
      a compound selected from the group consisting of:
         ((2R,3S,4R,5R)-5-(3-amino-5-methyl-1,4,5,6,8-pentaazaacenaphthylen-1(5H)-yl)-3,4-dihydroxytetrahydrofuran-2-yl)methyl dihydrogen phosphate;
         3-amino-5-(((2R,3R,4S,5R)-3,4-dihydroxy-5-(hydroxymethyl)tetrahydro-furan-2-yl)amino)-1-methylpyrimido[4,5-c]pyridazin-4(1H)-one; and
         ((2R,3S,4R,5R)-5-((3-amino-1-methyl-4-oxo-1,4-dihydropyrimido[4,5-c]pyridazin-5-yl)amino)-3,4-dihydroxytetrahydrofuran-2-yl)methyl dihydrogen phosphate.

13. The composition of claim 12, wherein the quantity of triciribine is present at a concentration of less than about 50 μM.

14. The composition of claim 12, further comprising an anticoagulant.

15. The composition of claim 12, wherein the donated red blood cells have biologically-relevant activity when transfused into a patient.

16. The composition of claim 1, wherein the donated blood or component thereof has biologically-relevant activity when transfused into a patient.

17. The composition of claim 8, wherein the donated plasma has biologically-relevant activity when transfused into a patient.

* * * * *